United States Patent
Venburg et al.

(10) Patent No.: US 8,349,768 B2
(45) Date of Patent: Jan. 8, 2013

(54) USE OF ABSCISIC ACID TO ALTER SENSORY CHARACTERISTICS OF WHITE GRAPES AND WINE

(75) Inventors: Gregory D. Venburg, Deerfield, IL (US); Andrew Rath, Box Hill (AU); Peter D. Petracek, Grayslake, IL (US)

(73) Assignee: Valent BioSciences Corporation, Libertyville, IL (US)

( * ) Notice: Subject to any disclaimer, the term of this patent is extended or adjusted under 35 U.S.C. 154(b) by 1284 days.

(21) Appl. No.: 12/011,821

(22) Filed: Jan. 30, 2008

(65) Prior Publication Data

US 2008/0254183 A1 Oct. 16, 2008

Related U.S. Application Data

(60) Provisional application No. 60/898,533, filed on Jan. 31, 2007.

(51) Int. Cl.
*A01N 31/02* (2006.01)
(52) U.S. Cl. ...................................... 504/162
(58) Field of Classification Search .................. 504/162
See application file for complete search history.

(56) References Cited

U.S. PATENT DOCUMENTS

2005/0198896 A1 9/2005 Quaghebeur

OTHER PUBLICATIONS

Dialog Search Nov. 22, 2010.*
Okamato et al. Effects of water deficit stress on leaf and berry ABA and berry ripening in Chardonnay. Vitis (2004) 43(1) pp. 15-17 Abstract.*
Regina et al. Comparative assessment of the physiological performance of grapevine cv. Chardonnay under normal conditions and under drought stress. REvista Brasileria de Fruticulture (1998) vol. 20, No. 2 pp. 135-144 (abstract).*
Regina et al. Gaseous exchanges in *Vitis vinifera*. Pesquisa Agropecuaria Brasilerir (1997) vol. 32, No. 6 pp. 579-584 Abstract.*
Jeong et al. "Effects of plant hormones and shading on the accumulation of anthocyanins and the expression of anthocyanin biosynthetic genes in grape berry skins." Plant Science 167 (2004) 247-252.*
Coombe, B. G. et al. "The Hormone Content of Ripening Grape Berries and the Effects of Growth Substance Treatments." Plant Physiol. (1973) vol. 51, 629-634.*
Bogs, J. et al. "Identification of the Flavonoid Hydroxylases from Grapevine and their regulation druing fruit development" Plant Physiology Jan. 2006 vol. 140 pp. 279-291.*
Byun et al., "Effects of GA3, thidiazuron and ABA on fruit set and quality of 'Kyoho' grapes" J. Kor. Soc. Hort. Sci., 1995, vol. 36, pp. 231-239.
Arana et al., "Maturity, variety and origin determination in white grapes (*Vitis vinifera* L.) Using near infrared reflectance technology", J. of Near Infrared Spectroscopy, 2005, vol. 13, Abstract Only.
Byun et al., (English Translation) "Effects of GA3, thidiazuron and ABA on fruit set and quality of 'Kyoho' grapes" J. Kor. Soc. Hort. Sci., 1995, vol. 36, pp. 231-239.
Downton et al., "Stomal closure fully accounts for the inhibition of photosynthesis by abscisic acid", New. Phytol. 1998, 108, pp. 263-266.
Extended European Search Report dated Sep. 26, 2011.
Cantos et al., "Varietal differences among the polyphenol profiles of seven table grape cultivars studied by LC-DAD-MS-MS", Journal of Agricultural and Food Chemistry, 2002, 50, pp. 5691-5696—XP007919425.
Wheeler, "The role of abscisic acid in grape berry development", pp. 1-175,—XP007919419, Oct. 2006.

* cited by examiner

*Primary Examiner* — Wendy C Haas
(74) *Attorney, Agent, or Firm* — Wood, Phillips, Katz, Clark & Mortimer

(57) ABSTRACT

This invention describes the use of S-abscisic acid (S-ABA) to modify sensory characteristics such as aroma, bouquet, flavor, mouthfeel, astringency, balance, complexity or finish of white grapes and white wine.

6 Claims, No Drawings

USE OF ABSCISIC ACID TO ALTER SENSORY CHARACTERISTICS OF WHITE GRAPES AND WINE

FIELD OF THE INVENTION

The present invention is directed to the use of S-abscisic acid and its salts to modify the development of the sensory characteristics of white grapes and white wine, such as aroma, bouquet, flavor, mouthfeel, astringency, balance, complexity or finish.

BACKGROUND OF THE INVENTION

Abscisic acid (S-abscisic acid, S-ABA, ABA) is a naturally occurring plant hormone found in all higher plants (Cutler and Krochko. 1999. Trends in Plant Science. 4: 472-478. Finkelstein and Rock. 2002. The Arabidopsis Book. ASPB, Monona, Md., 1-52). S-ABA is involved in many major processes during plant growth and development including dormancy, germination, bud break, flowering, fruit set, general growth and development, stress tolerance, ripening, maturation, organ abscission and senescence. S-ABA also plays an important role in plant tolerance to environmental stresses, such as drought, cold, and excessive salinity.

One key role of S-ABA in regulating physiological responses of plants is to act as a signal of reduced water availability to reduce water loss, inhibit growth and induce adaptive responses. All these functions are related to stomatal closure of plant leaves (Raschke and Hedrich, 1985, Planta, 163: 105-118). When stomata close, plants conserve water to survive in environmental stresses. However, stomatal closure also results in the reduction of photosynthesis, and respiration and thus growth. Stomatal closure is a rapid response of plants to S-ABA. The mechanism of S-ABA that causes stomatal closure has been studied, and the effect has been shown to be due primarily to S-ABA's effect on guard cell ion channels. Specifically, S-ABA blocks $H^+$ extrusion and $K^+$ influx from guard cells and promotes $K^+$, $Cl^-$, and malate extrusion and $Ca^{2+}$ influx. The net effect of S-ABA is to reduce the total osmotica in the guard cells, which in turn decreases the water content in the cell. This causes the guard cells to lose their turgor and thus close the stomata (Assmann 2004 In: *Plant Hormones Biosynthesis, Signal Transduction, Action!* ed. Davies, p 391-412). The closing of stomata results in reduced transpiration of the plant leaf. In grapes, application of S-ABA has been reported to increase stomatal resistance in grapevines, thereby reducing the gas exchange and stomatal transpiration of the leaves (During and Broquedis, 1980, Sci. Hort., 13: 253-260).

The exogenous application of S-ABA to red grapes prior to harvest has been shown to increase the accumulation of anthocyanins and increase the red color of the grape berry skins (e.g. Han, D. H, S. M. Lee, and S. B. Kim. 1996, J. Kor. Soc. Hort. Sci. 37: 416-420; Lee, K. S., J. C. Less, Y. S. Hwang, and I. B. Hur, 1997, J. Kor. Soc. Hort. Sci. 38: 717-721; Kondo, S., Masuda, E. and Inoue, K., 1998, Acta Hort., 464: 35-40; Pepe, M. C., Fidelibus, M. W., Dokoozlian, N. 2006, HortScience, 41:1440-1445).

The sensory characteristics of wine, such as aroma and flavor, are complex and there is interest in altering wine grape berry and/or wine characteristics to produce more diverse or better wine or wines with different balances of sensory characteristics. A patent application has been filed (Quaghebeur, K., 2005, US 2005/0198896 A1) claiming that ABA application enhances wine quality as a consequence of simulating drought in the grapevine leading to reduction in grape berry size in conjunction with increased sugar content. However, no mention is made of ABA application affecting sensory characteristics such as aroma, bouquet, flavor, mouthfeel, astringency, balance, complexity, and finish. The literature reports that the effect of S-ABA application on grapes is to increase berry and cluster weight (Han, D. H, S. M. Lee, and S. B. Kim. 1996. J. Kor. Soc. Hort. Sci. 37: 416-420). While the effect of S-ABA to increase red color of red grapes has been studied and reported, there are no previous reports on the effect of and the use of S-ABA on white grapes to affect the various sensory characteristics of white grapes and/or the resulting wine.

SUMMARY OF THE INVENTION

The present invention is directed to the preharvest treatment of white wine grapes with S-ABA or its salts after fruit set. This treatment alters the development of white grape berry and wine sensory characteristics, such as aroma, bouquet, flavor, mouthfeel, astringency, balance, complexity or finish. Manipulation of these factors can help achieve the wine style desired by the viticulturist and winemaker.

DETAILED DESCRIPTION OF THE INVENTION

The present invention comprises the application of S-ABA or its salts to white grape grapevines to modify development of grape berry and wine sensory characteristics. S-ABA or a salt of S-ABA is applied to the grapevines as a foliar spray to the grape berries and leaves, by application to the roots of the grapevine through irrigation or fertigation methods, or by injection of S-ABA into the grapevine.

Abscisic acid (S-ABA; ABA; S-(+)-abscisic acid; +-ABA, (+)-(S)-cis,trans-abscisic acid, (+)-(S)-cis,trans-ABA; (S)-5-(1-hydroxy-2,6,6,-trimethyl-4-oxo-2-cyclohexen-1-yl)-3-methyl-(2Z,4E)-pentadienoic acid; CAS registry no. [21293-29-8]) is available from Lomon BioTechnology Co., Ltd. (Shichuan, China).

Suitable salts of S-ABA include, but are not limited to sodium, potassium, calcium, ammonium, magnesium and amine salts.

S-ABA or its salts is applied to the grapevines after berry set to achieve the desired effect on the sensory characteristics of the grape berries and wine. The presently preferred timing of the S-ABA application is during the period of pre-veraison (approximately 3 weeks before veraison, where veraison is defined as berry softening) through the post-veraison period (when sugar levels in berries measure approximately 18-20° brix (10-11 Baume)).

Water is used as the carrier solvent for the applications. In the present invention, surfactants can be added to the chemical solution to improve the performance of the S-ABA or its salts, particularly for foliar application. The water solution may contain between 0.01% to 0.5% v/v of a surfactant, such as Tween 20 (available from Sigma-Aldrich, St. Louis, Mo.).

The presently preferred surfactant for S-ABA or S-ABA salt performance is Brij 98 (polyoxyethylene (20) oleyl ether) available from Uniqema (Castle, Del.). Other surfactants are also useful in the present invention, including but not limited to, other surfactants in the Brij family (polyoxyethylene fatty alcohol ether) available from Uniqema (Castle, Del.), surfactants in the Tween family (Polyoxyethylene sorbitan ester) available from Uniqema (Castle, Del.), the Silwet family (Organosilicone) available from Momentive Performance Materials (Wilton, Conn.), the Triton family (Octylphenol ethoxylate) available from The Dow Chemical Company (Midland, Mich.), the Tomadol family (ethoxylated linear alcohol) available from Tomah3 Products, Inc. (Milton, Wis.), the Myrj family (Polyoxyethylene (POE) fatty acid ester) available from Uniqema (Castle, Del.), the Span family (Sorbitan ester) available from Uniqema (Castle, Del.), and the Trylox family (Ethoxylated Sorbitol and Ethoxylated Sorbitol Ester) available from Cognis Corporation (Cincinnati, Ohio) as well as commercial surfactants such as Latron B-1956 (77.0% modified phthalic/glycerol alkyl resin and 23.0% Butyl alcohol) available from Dow AgroSciences LLC (Indianapolis, Ind.), Caspil (Blend of Polyether-polymethyl-siloxanecopolymer and nonionic surfactant) available from Aquatrols (Paulsboro, N.J.), Agral 90 (Nonyl phenol ethoxylate) available from Norac Concept. Inc. (Orleans, Ontario, Canada), Kinetic (99.00% proprietary blend of polyalkyleneoxide modified polydimethylsiloxane and nonionic surfactants) available from Setre Chemical Company (Memphis, Tenn.), and Regulaid (90.6% 2-butoxyethanol, poloxalene, monopropylene glycol) available from KALO, Inc. (Overland Park, Kans.).

Other additives are also useful in the present invention including, but not limited to, urea, nitrate salts such as ammonium nitrate, salts such as calcium chloride, humectants such as poly(ethylene glycol) and vegetable oils such as soybean oil, corn oil, cotton oil and palm oil.

The effective concentration range of the active ingredient S-ABA varies depending on the water volume applied as well as other factors such as the plant variety, height, age, desired duration of effect and application method. The S-ABA concentration range is from about 1-about 10,000 ppm S-ABA. The preferred S-ABA concentration range for foliar applications is about 50-about 500 ppm. The preferred application volume for foliar applications is about 25-about 300 gallons/A. Foliar spray applications are directed at the grape bunches to achieve complete coverage of the grape bunches and to maximize the effect of the S-ABA application. Soil applications are directed towards the rooting zone. Application methods include, but are not limited to application through irrigation/fertigation dripper line or application of S-ABA formulations or solutions to the soil at the base of the vine, followed by application of water to the soil to transport the S-ABA to the roots of the vine.

The invention is illustrated by following representative examples.

EXAMPLES

Example 1

A replicated field experiment was conducted on the white wine grape cultivar 'Semillon' in the Riverina growing region of New South Wales, Australia to test the effect of S-ABA on white grapes. Four treatments were tested: Untreated control, 200 ppm S-ABA applied at pre-veraison, 200 ppm S-ABA applied at veraison, and 200 ppm S-ABA applied during the post-veraison period (berry sugar level of 10-11 Baume (18-20° brix)). There were 4 replicates of each treatment and the experiment was laid out in a randomized complete block (RCB) design. S-ABA was applied using a commercial airblast sprayer. S-ABA was applied at a concentration of 200 ppm in a volume of approximately 2000 L/Ha (approximately 200 gallons/A) in order to achieve thorough and complete coverage of the grape bunches. A 20% S-ABA soluble granule formulation was utilized in the experiment. The commercial surfactant Agral was included at a rate of 10 ml/100 L spray. Applications of S-ABA were made at pre-veraison (approximately 3 weeks before veraison or berry softening), veraison, and during the post-veraison period when the grape sugar levels had reached approximately 10-11 Baume (18-20° brix). The 10-11 Baume application took place 36 days after the veraison application. Irrigation, summer pruning, insecticide/fungicides and other routine vine management practices were the same as those practiced commercially by the grower in the adjacent parts of the vineyard.

A panel of three tasters was able to discern notable differences in flavor between the S-ABA treated grapes and the untreated grapes sampled at both preharvest and at harvest.

Grape samples were harvested at the time of commercial harvest for berry analysis and table wine production. For the standard maturity berry measurements, 12-20 bunches per replicate were sampled. Bunches were randomly selected from both sides of the vines. Samples were analyzed using standard analytical methods used by the grape and wine industry. For additional spectral analyses, samples of 100 berries from each treatment were collected prior to winemaking.

S-ABA did not consistently affect Semillon berry sugar content (Baume), pH, titratable acidity (Table 1) or bunch weight (bunch weight increased with time). Chemical analysis indicated some differences in total phenolics, hydroxycinnamates, total flavonoids, and estimated brown pigments. Phenolic compounds are responsible for color and flavor of fresh fruits and processed products. Hydroxycinnamates are believed to contribute to bitterness and other flavors in wine. The results indicate that the S-ABA treatments did not have consistent effects on the typical grape maturity/quality measurements.

TABLE 1

Effect of S-ABA on Baume, pH, and titratable acidity of Semillon berries at Harvest (March 8, 54 days after veraison).

| Treatment | Baume | pH | Titratable Acidity |
|---|---|---|---|
| Untreated Control | 11.8 | 3.63 | 4.1 |
| Pre-veraison | 11.6 | 3.57 | 4.5 |
| Veraison | 11.7 | 3.56 | 4.5 |
| Post-veraison (11 Baume) | 11.6 | 3.61 | 4.0 |

The S-ABA treatments tended to increase the phenolic composition of the berries (Table 2).

TABLE 2

Effect of S-ABA on spectral analysis and total phenolics, hydroxycinnamates, flavonoids, and brown pigments of Semillon berries at harvest.

| Treatment | A420 | A320 | A280 | Total Phenolics (a.u.) | Total Hydroxy-cinnamates (a.u.) | Total Flavonoids (a.u.) | Est. of brown pigments (a.u.) |
|---|---|---|---|---|---|---|---|
| Untreated Control | 0.358 | 2.614 | 6.44 | 2.44 | 1.21 | 1.64 | 0.36 |

TABLE 2-continued

Effect of S-ABA on spectral analysis and total phenolics, hydroxycinnamates, flavonoids, and brown pigments of Semillon berries at harvest.

| Treatment | A420 | A320 | A280 | Total Phenolics (a.u.) | Total Hydroxy-cinnamates (a.u.) | Total Flavonoids (a.u.) | Est. of brown pigments (a.u.) |
|---|---|---|---|---|---|---|---|
| Pre-veraison | 0.465 | 2.642 | 6.62 | 2.62 | 1.24 | 1.80 | 0.47 |
| Veraison | 0.471 | 2.713 | 6.85 | 2.85 | 1.31 | 1.98 | 0.47 |
| Post-veraison (11 Baume) | 0.461 | 2.59 | 6.47 | 2.47 | 1.19 | 1.68 | 0.46 |

Wine Production:

Wine was produced from the grapes from each of the S-ABA treatments. Small lot primary fermentations were conducted and the wine was bottled. Triplicate ferments of each treatment were conducted using approximately 3×50 kg of grapes. Each replicate ferment contained an equal volume of grapes from each of the four field replicates. Grapes were harvested from the central panels within each replicate. All grapes were harvested from both sides of the vines from these panels. The grapes were transferred immediately to the experimental winery, protected from heat and treated with sulfur dioxide. A standard winemaking protocol used for small-scale replicated primary fermentations was followed. Following the fermentation, the wine was bottled.

Wine Analysis:

Chemical analyses were conducted on the wines prepared from the various treatments in the field experiment using industry standard analytical methods.

Spectral analysis indicated that the S-ABA treated wines had higher levels of hydroxycinnamates (Table 3).

TABLE 3

Effect of S-ABA on total hydroxycinnamates of Semillon wine.

| Treatment | Total Hydroxycinnamates (a.u.) | Std. Dev. |
|---|---|---|
| Untreated Control | 0.7600 | 0.04243 |
| Pre-veraison | 0.8700 | 0.05292 |
| Veraison | 0.9033 | 0.05686 |
| Post-veraison (11 Baume) | 0.8267 | 0.06429 |

Untreated control vs. veraison: P = 0.0604

Sensory analysis was conducted on the treated and untreated wines. A panel consisting of nine experienced wine tasters evaluated the wines for aroma and taste. The wine grape cultivar was identified, but no information regarding the field treatments was identified to the tasters.

A straight judgment of difference test was conducted to determine if the wines were different from the untreated control. All Semillon wines prepared from the S-ABA treatments were judged to be different from the reference wine (untreated control) with statistical significance. Therefore, these wines can be considered to be different from the reference wine, thereby implying a treatment effect.

Table 4 shows the number of experienced wine tasters who determined Semillon wines from various S-ABA treatments to be different from the reference wine (untreated control) with probabilistic significance.

TABLE 4

Effect of S-ABA on differences of Semillon wine.

| | Number of tasters who selected as different from reference wine/Total number of tasters | Statistically significant |
|---|---|---|
| Untreated Control (reference) | — | — |
| Pre-veraison | 8/9 | Yes |
| Veraison | 8/9 | Yes |
| Post-veraison (11 Baume) | 8/9 | Yes |

A wine descriptive analysis was also conducted for the Semillon wines prepared from the untreated control and from the S-ABA treatments. The panels provided descriptive terms to characterize the aroma, taste and color profile of each wine. The methodology used was based on survey-style collection with a thematic analysis to pull out the most consistent terms (Table 5).

TABLE 5

Effect of S-ABA on Semillon wine characteristics. Descriptor of aroma, taste, and color for each reference wine and each significantly different from the reference.

| Treatment | Aroma | Taste | Color |
|---|---|---|---|
| Untreated | Low aroma, some fruit | Citrus, acidic | Pale straw |
| Pre-veraison | More intense fruit | Much more acidic | Pale straw |
| Veraison | More intense fruit | Slightly more citrus and acidic | Slightly darker pale straw |
| Post-veraison (11 Baume) | More intense fruit | Moderately more fruity and acidic | Pale straw |

The results of this experiment demonstrate that the application of S-ABA to the white wine grape cultivar 'Semillon' modifies the sensory characteristics of both the grapes and resulting wine. The S-ABA treatments increased or intensified the fruit aroma and acidic taste of the wine.

Example 2

A large block unreplicated field experiment was conducted on the white wine grape cultivar 'Chardonnay' in the Riverina growing region of New South Wales, Australia to test the effect of S-ABA on white grapes. Three treatments were tested: Untreated control, 200 ppm S-ABA applied at pre-veraison and 200 ppm S-ABA applied at veraison. Each block consisted of 4 rows and covered 0.4 Ha in size. S-ABA was applied using a commercial airblast sprayer. S-ABA was applied at a concentration of 200 ppm in a volume of approximately 1000 L/Ha (approximately 100 gallons/A) in order to achieve thorough and complete coverage of the grape bunches. A 20% S-ABA soluble granule formulation was utilized in the experiment. The commercial surfactant Kendeen 20 was included at a rate of 50 ml/100 L spray. Applications of S-ABA were made at pre-veraison (approximately 3 weeks before veraison or berry softening) and veraison. Irrigation, summer pruning, insecticide/fungicides and other routine vine management practices were the same as those practiced commercially by the grower in the adjacent parts of the vineyard.

A panel of two tasters was able to discern notable differences in flavor between the S-ABA treated grapes and the untreated grapes sampled at both preharvest and at harvest.

Grapes samples were harvested at the time of commercial harvest for berry analysis and table wine production. For the standard maturity berry measurements, 12-20 bunches per replicate were sampled. Bunches were randomly selected from both sides of the vines. Samples were analyzed using standard analytical methods used by the grape and wine industry. For additional spectral analyses, samples of 100 berries from each treatment were collected prior to winemaking.

S-ABA did not consistently affect Chardonnay berry sugar content (Baume), pH, titratable acidity (Table 6) or bunch weight. Chemical analysis indicated some differences in total phenolics, hydroxycinnamates, total flavonoids, and estimate of brown pigments (Table 7). Phenolic compounds are responsible for color and flavor of fresh fruits and processed products. Hydroxycinnamates are believed to contribute to bitterness and other flavors in wine. The results indicate that the S-ABA-treatments did not have consistent effects on the typical maturity/quality measurements taken on the grapes.

TABLE 6

Effect of S-ABA on Baume, pH, and titratable acidity of Chardonnay berries at Harvest (February 5, 26 days after veraison).

| Treatment | Baume | pH | Titratable Acidity |
|---|---|---|---|
| Untreated Control | 14.4 | 3.57 | 6.4 |
| Pre-veraison | 14.3 | 3.73 | 6.2 |
| Veraison | 14.4 | 3.60 | 6.9 |

TABLE 7

Effect of S-ABA on spectral analysis and total phenolics, hydroxycinnamates, flavonoids, and brown pigments of Chardonnay berries at harvest.

| Treatment | A420 | A320 | A280 | Total Phenolics (a.u.) | Total Hydroxy-cinnamates (a.u.) | Total Flavonoids (a.u.) | Est. of brown pigments (a.u.) |
|---|---|---|---|---|---|---|---|
| Untreated Control | 0.535 | 3.50 | 18.36 | 14.36 | 2.10 | 12.97 | 0.535 |
| Pre-veraison | 0.530 | 3.53 | 17.37 | 13.37 | 2.13 | 11.96 | 0.530 |
| Veraison | 0.567 | 3.38 | 14.07 | 10.07 | 1.98 | 8.76 | 0.567 |

Wine Production:

Wine was produced from the grapes from each of the S-ABA treatments. Small lot primary fermentations were conducted and the wine was bottled. Duplicate ferments of each treatment were conducted using approximately 3×50 kg of grapes. Each replicate ferment contained an equal volume of grapes from entire panels of vines. All grapes were harvest from both sides of the vines from these panels. The grapes were transferred immediately to the experimental winery, protected from heat and treated with sulfur dioxide. A standard winemaking protocol used for small-scale replicated primary fermentations was followed. Following the fermentation, the wine was bottled.

Wine Analysis:

Chemical analyses were conducted on the wines prepared from the various treatments in the field experiment using industry standard analytical methods.

Spectral analysis indicated that the S-ABA treated wines had a different balance of hydroxycinnamates and phenolics (Table 8).

TABLE 8

Effect of S-ABA on total phenolics and hydroxycinnamates of Chardonnay wine.

| Treatment | Total Phenolics (a.u) | Total Hydroxycinnamates (a.u) |
|---|---|---|
| Untreated Control | 2.87 | 3.28 |
| Pre-veraison | 2.55 | 3.14 |
| Veraison | 2.97 | 3.19 |

Sensory analysis was conducted on the S-ABA-treated and untreated wines. A panel consisting of ten experienced wine tasters evaluated the wines for aroma and taste. The wine grape cultivar was identified, but no information regarding the field treatments was identified to the tasters.

A straight judgment of difference test was conducted to determine if the wines were different from the untreated control. All Chardonnay wines prepared from the S-ABA treatments were judged to be different from the reference wine (untreated control) with statistical significance. Therefore, these wines can be considered to be different from the reference wine, thereby implying a treatment effect.

A wine descriptive analysis was also conducted for the Chardonnay wines prepared from the untreated control and from the S-ABA treatments. The panels provided descriptive terms to characterize the aroma and taste profile of each wine. The methodology used was based on survey-style collection with a thematic analysis to pull out the most consistent terms (Table 9).

TABLE 9

Effect of S-ABA treatment on Chardonnay wine characteristics.
Descriptor of aroma, taste, and color for each reference wine
and each significantly different from the reference.

| Treatment | Descriptive characteristics compared to the Untreated |
| --- | --- |
| Pre-veraison | More intense aroma, slightly more mineral and bitterness |
| Veraison | More aroma: spice, citrus, pineapple, pea; More acidic, less astringent. Increased complexity. |

The results of this experiment demonstrate that the application of S-ABA to the white wine grape cultivar 'Chardonnay' modifies the sensory characteristics of both the grapes and resulting wine. The S-ABA treatments increased or intensified the fruit aroma and acidic taste in the wine.

The invention claimed is:

1. A method of modifying white grape berry and wine sensory characteristics, such as aroma, bouquet, flavor, mouthfeel, astringency, balance, complexity or finish, by application of from about 50 ppm to about 500 ppm S-abscisic acid or its salts to white grapes or grapevines after fruit set.

2. The method of claim 1 wherein the white grapes are Semillon grapes.

3. The method of claim 1 wherein the white grapes are Chardonnay grapes.

4. A method of intensifying fruit flavor and aroma of white grape berry and wine sensory by application of from about 50 ppm to about 500 ppm S-abscisic acid or its salts to white grapes or grapevines after fruit set.

5. The method of claim 4 wherein the white grapes are Semillon grapes.

6. The method of claim 4 wherein the white grapes are Chardonnay grapes.

* * * * *